US00RE37088E

(19) United States
(12) Reissued Patent
Olstad et al.

(10) Patent Number: US RE37,088 E
(45) Date of Reissued Patent: Mar. 6, 2001

(54) METHOD FOR GENERATING ANATOMICAL M-MODE DISPLAYS

(75) Inventors: Bjorn Olstad, Ranheim; Eivind Holm, Horten, both of (NO); James Ashman, Braunstone (GB)

(73) Assignee: Vingmed Sound A/S, Horten (NO)

(21) Appl. No.: 09/078,378

(22) Filed: May 13, 1998

Related U.S. Patent Documents

Reissue of:
(64) Patent No.: 5,515,856
Issued: May 14, 1996
Appl. No.: 08/379,205
Filed: Jan. 27, 1996

(30) Foreign Application Priority Data

Aug. 30, 1994 (NO) ..... 94.3214

(51) Int. Cl.[7] ..... A61B 8/00
(52) U.S. Cl. ..... 600/440
(58) Field of Search ..... 600/440, 441, 600/463, 454, 455, 448, 449, 450, 451, 453, 456

(56) References Cited

U.S. PATENT DOCUMENTS

| | | | |
|---|---|---|---|
| 3,955,561 | 5/1976 | Eggleton | 128/2.05 Z |
| 4,271,842 | 6/1981 | Specht et al. | 128/661 |
| 4,413,521 | 11/1983 | Van Kemenade | 73/626 |
| 4,501,277 | 2/1985 | Hongo | 128/660 |
| 4,735,211 | 4/1988 | Takasugi | 128/660 |
| 4,932,414 | 6/1990 | Coleman et al. | 128/660 |
| 5,097,836 | 3/1992 | Yamada et al. | 128/660 |
| 5,105,813 | 4/1992 | Shikata | 128/660 |
| 5,127,409 | 7/1992 | Daigle | 128/660 |
| 5,195,521 | 3/1993 | Melton, Jr. et al. | 128/660 |
| 5,285,788 | 2/1994 | Arenson et al. | 128/660 |
| 5,355,887 | 10/1994 | Iizuka et al. | 128/660.04 |
| 5,375,599 | 12/1994 | Shimizu | 128/660.04 |

OTHER PUBLICATIONS

Foley, et al., "Computer Graphics: Principles And Practice," Addison Wesley USA (1990) (only bibliographic pages included).

Olstad, B., "Maximizing Image Variance In Rendering Of Columetric Data Sets", Journal Of Electronic Imaging, 1:256–265, Jul. 1992.

Borgefors, G., "Distance Transformations In Digital Images"., Computer Vision, Graphics And Image Processing 34, 1986, pp. 344–371.

Seitz, P., "Optical Superresolution Using Solid State Cameras And Digital Signal Processing", Optical Engineering 27(7) Jul. 1998, pp. 535–540.

R. Omoto, Y. Yokote, et al. "B/M Conversion System With Free Setting Of Cursor Line: Clinical Applications Thereof", 41–PA–31, 3pgs. (Saitama Medical School).

(List continued on next page.)

*Primary Examiner*—George Manuel
(74) *Attorney, Agent, or Firm*—Blakely, Sokoloff, Taylor & Zafman, LLP

(57) ABSTRACT

A method for generating anatomical M-Mode displays for ultrasonic investigation of living biological structures during movement of the structure, for example a heart function, employing an ultrasonic transducer (21) comprises the acquisition of a time series of 2D or 3D ultrasonic images (22), arranging said time series so as to constitute data sets, providing at least one virtual M-Mode line (23) co-registered with said data sets, subjecting said data sets to computer processing on the basis of said at least one virtual M-Mode line, whereby interpolation along said at least one virtual M-Mode line is effected, and displaying the resulting computed anatomical M-Mode display (24) on a display unit.

50 Claims, 5 Drawing Sheets

OTHER PUBLICATIONS

R. Omoto, Y. Yokote, et al. "New System for Converting From Tomogram Echocardiography To M–Mode Freely Set Cursor Line", 40–C–51, 2pgs. (Saitama Medical School).

"New Transforming System From Tomogram Echocardiography To M–Mode", 40–C–5.1, 7pgs.

R. Omoto, Y. Yokote, et al. "B/M Conversion System with Free Setting of Cursor Line: Clinical Applications Thereof", 41–PA–31, 3pp.

R. Omoto, Y. Yokote, et al. "New System For Converting From Tomogram Echocardiography To M–Mode Freely Set Cursor Line", 40–C–51, 2pp.

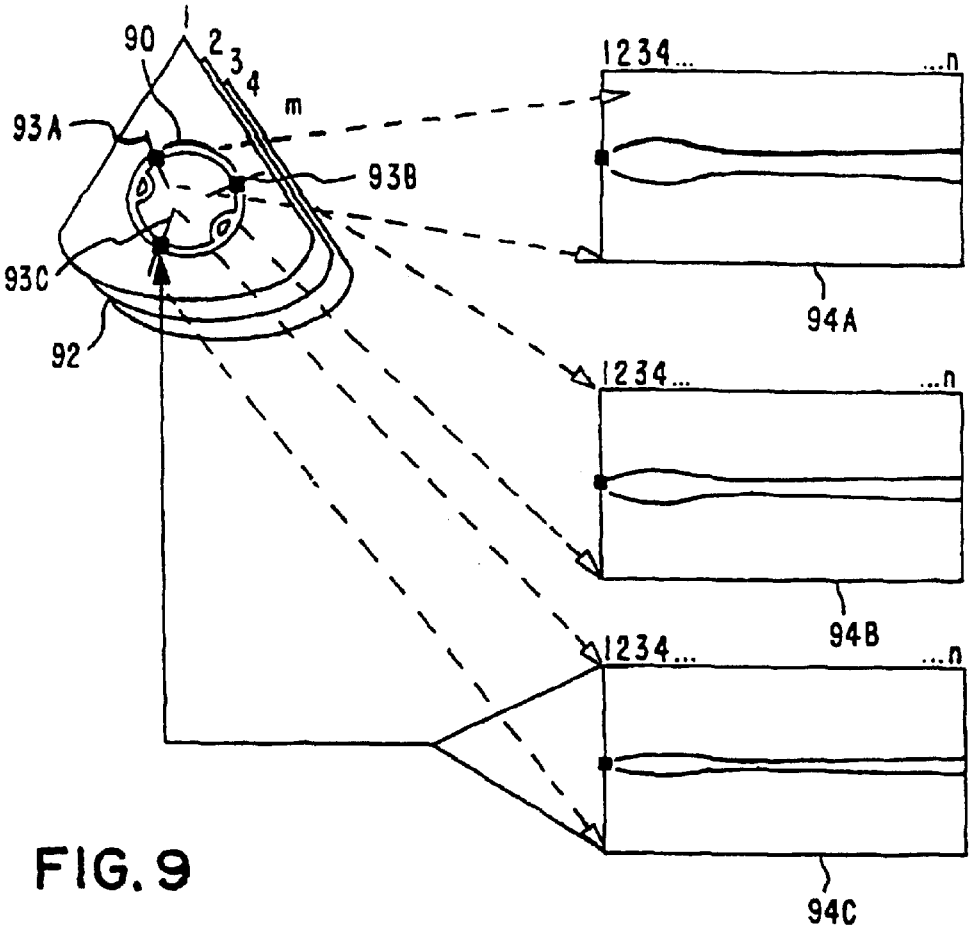
FIG. 9
FIG. 10
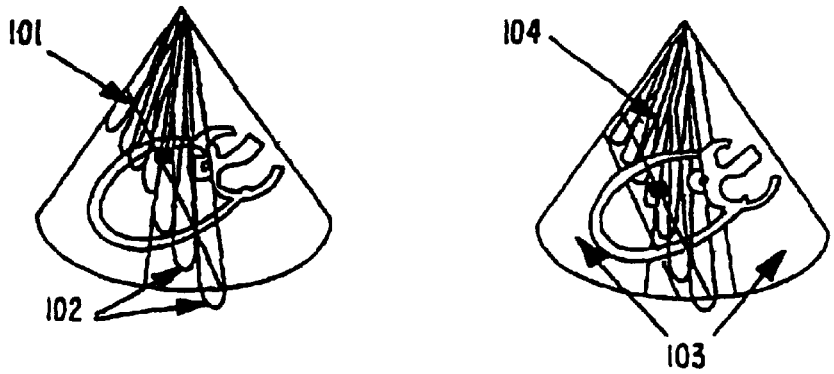

METHOD FOR GENERATING ANATOMICAL M-MODE DISPLAYS

Matter enclosed in heavy brackets [ ] appears in the original patent but forms no part of this reissue specification; matter printed in italics indicates the additions made by reissue.

BACKGROUND OF THE INVENTION

This invention relates to a method for generating anatomical M-Mode displays in ultrasonic investigation of living biological structures during movement, for example a heart function, employing an ultrasonic transducer.

The invention describes a technique for obtaining anatomically meaningful M-Mode displays by data extraction from 2D (two dimensional) and 3D (three dimensional) ultrasonic imaging. Conventional M-Mode is acquired along one acoustical beam of an ultrasonic transducer employed, displaying the [tide-variant] *time-variant* data in a display unit with time along the x-axis and depth along the y-axis. The localization of the M-Mode line in conventional M-Mode is limited to the set of beam directions that can be generated (scanned) by the transducer.

In cardiology, the use of the M-Mode method is fairly standardized, requiring specific cuts through the heart at standard positions and angles. To be able to perform a good M-Mode measurement, important criteria are:

1. Image quality. The borders and interfaces between different structures of the heart must be clearly visible. One of the most important factors to achieve this, is to position the ultrasound transducer on the body concerned at a point where the acoustic properties are optimum. These places are often referred to as "acoustic windows". On older patients, these windows are scarce, and hard to find.
2. Alignment. The standardized M-Mode measurements require that the recording is taken at specific angles, usually 90 degrees relative to the heart structure being investigated.
3. Motion. As the heart moves inside the chest during contraction and relaxation, a correct M-Mode line position at one point in the heart cycle may be wrong at another point in the same heart cycle. This is very difficult to compensate for manually, since the probe must be moved synchronous to the heartbeats. Therefore, most sonographers settle for a fixed, compromise direction of the M-Mode line, i.e. transducer beam.
4. Wall thickening analysis. With coronary diseases, an important parameter to observe is the thickening of the left ventricular muscle at various positions.

In many cases there can be problems getting the correct alignment at a good acoustical window. Often, the good acoustic windows give bad alignment, and vice versa. Hence, the sonographer or user spends much time and effort trying to optimize the image for the two criteria (alignment, image quality).

SUMMARY OF THE INVENTION

With the advent of high-performance digital front-end control for phased transducer array probes, the possibility exists for acquiring 2D images at very high framerates (<10 ms per 2D image). These 2D data are stored in a computer RAM, with storage capacity enough to hold one or more full heart cycles worth of 2D data recordings. M-Mode displays can be generated based on these recordings with an adequate temporal resolution. According to the present invention this allows for complete flexibility in the positioning of the M-Mode lines. The invention describes how this flexibility can be utilized to improve the anatomical information content in the extracted M-Mode displays.

The invention also applies to extraction of M-Mode displays from a time series with 3D images. In 3D it is possible to compensate for the true 3D motion of the ventricle. Based on 2D recordings the operator will be limited to compensate for the movements that can be measured in the imaged plane. The invention also describes how local M-Mode information extracted from 3D acquisitions can be utilized to obtain a color encoding of the ventricle wall providing information about wall thickening.

The anatomical M-Mode displays can be generated in real-time during scanning of a 2D image or during real-time volumetric scanning. The invention then describes how multiple M-Mode displays can be maintained together with the live 2D or 3D image. These M-Mode displays can also be freely positioned and even allowed to track the location and direction of the ventricle wall during the cardiac cycle. During real-time scanning, time resolution of anatomical M-Mode displays may be increased by constraining the 2D or volumetric scanning to the area defined by the ultrasound probe and the M-Mode line. This requires complete control of the ultrasound scanner front-end.

The anatomical M-Mode can also be used as a post-processing tool, where the user acquires the 2D/3D image sequence at super-high framerates, without making any M-Mode recordings. As long as the 2D data includes an adequate cut/view through the heart, the user may use the anatomical M-Mode to do the M-Mode analysis later.

The computer processing of data sets are previously known, as for example described in: J. D. Foley, A van Dam, S. K. Seiner, J. F. Hughes "Computer Graphics: Principles and Practice", Addison Wesley U.S.A. (1990). Among other things line drawing algorithms are described in this reference. Thus, such computer processing, operations and steps are not explained in detail in the following description. Other references relating more specifically to techniques of particular interest here are the following:

B. Olstad, "Maximizing image variance in rendering of volumetric data sets," Journal of Electronic Imaging, 1:245–265, July 1992.

E. Steen and B. Olstad, "Volume rendering in medical ultrasound imaging". Proceedings of 8th Scandinavian Conference on Image Analysis. Tromsø, Norway May 1993.

G. Borgefors, "Distance transformations in digital images", Computer vision, graphics and image processing 34, 1986, pp. 344–371.

Peter Seitz, "Optical Superresolution Using Solid State Cameras and Digital Signal Processing", Optical Engineering 27(7) July 1988.

On the background of known techniques this invention takes as a starting-point methods for computation of conventional M-Mode and established clinical procedures for utilization of M-Mode imaging. The invention includes new techniques for the computation of anatomical M-Mode displays based on a time series of 2D or 3D ultrasonic images. The anatomical M-Mode is derived as a virtual M-Mode measurement along an arbitrary or virtual, tilted M-Mode line. What is novel and specific in the method according to the invention is defined more specifically in the appended claims.

Some of the advantages obtained with this invention can be summarized as follows: Multiple M-Mode displays with arbitrary positioning can be computer on the basis of a 2D or 3D acquisition. The position of the M-Mode line is not limited to the scanning geometry and can be freely positioned. Global heart movements can be compensated for by moving the M-Mode line according to the motion of the heart during the cardiac cycle. Wall thickening analysis is improved due to the possibility of keeping the M-Mode line perpendicular to the ventricle wall during the entire cardiac cycle. Reference points in the scene can be fixed at a given y-coordinate in the M-Mode display, hence improving the visual interpretability of relative motion/thickening phenomenons. 3D acquisitions can be visualized by mapping properties extracted from local M-Mode lines in a color encoding of the ventricle wall.

BRIEF DESCRIPTION OF THE DRAWINGS

The invention shall be described in more detail in the following description of various embodiments with reference to the drawings, in which:

FIG. 9 schematically illustrates how a color encoding of the ventricle wall representing wall thickening can be computed in 4D ultrasonic imaging.

FIG. 10 schematically illustrates how the acquisition of the ultrasound data can be optimized for used in anatomical M-Mode, reducing the amount of data used for each image, enabling more images to be acquired during a given time span.

DESCRIPTION OF THE PREFERRED EMBODIMENTS

Figure 1:
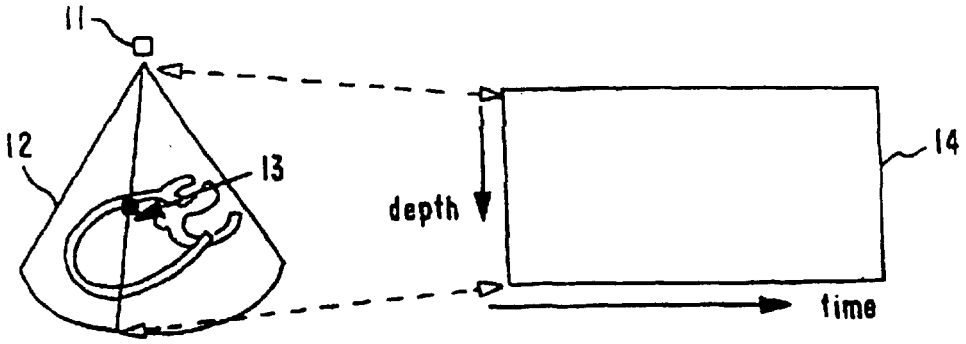
FIG. 1 PRIOR ART
FIG. 1 schematically illustrates the computation of M-Mode displays according to the prior art.

FIG. 1 illustrates conventional M-Mode imaging. An ultrasound transducer 11 is schematically indicated in relation to an ultrasonic image 12 obtained by angular scanning of the acoustical beam of the transducer. In this conventional method by the M-Mode line or corresponding acoustical beam 13 is fixed at a given position and the ultrasonic signal along the beam is mapped as a function of time in the M-Mode display 14. Extreme temporal resolution can be achieved with this prior art because a new time sample can be generated as soon as the data for one beam has been gathered. This prior art for M-Mode imaging will on the other hand limit the positioning of the M-Mode line 13 according to the acoustic windows and scanning geometry.

TILTED M-MODE LINES

Figure 2:
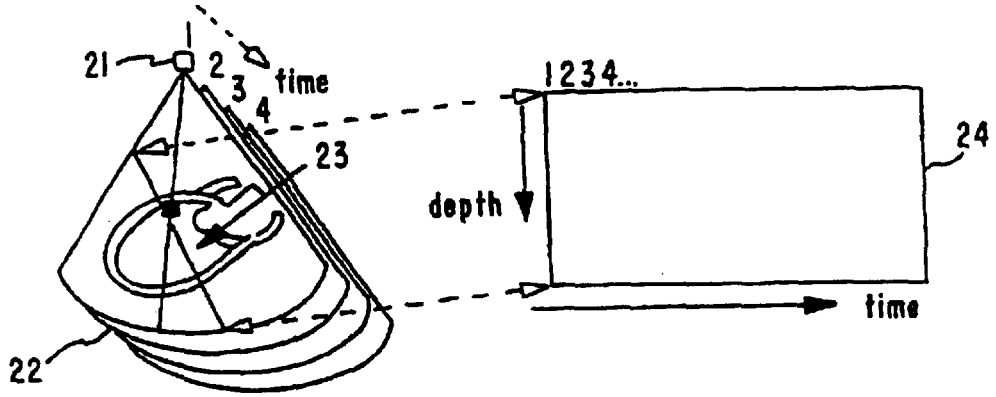
FIG. 2 schematically illustrates the inventive concept of a tilted anatomical or virtual M-Mode line for computation of corresponding M-Mode displays.

This invention relates to how M-Mode images can be generated by extraction of interpolated displays from time series of 2D or 3D images. The concept of a "tilted" M-Mode display 24 is illustrated in FIG. 2. The "virtual" M-Mode line 23 is in this case freely moveable, not being restricted to coincide with one acoustic beam (transducer 21) originating at the top of the 2D image(s) 22.

MULTIPLE M-MODE LINES

Figure 3:
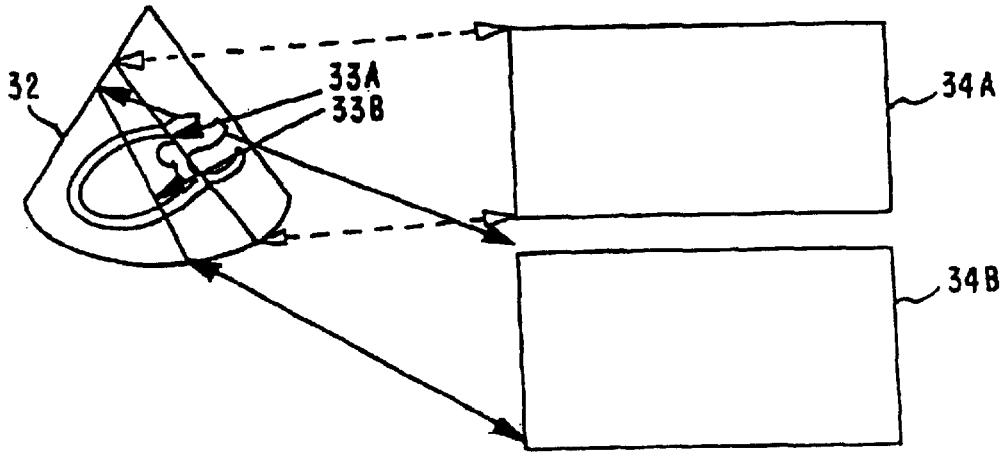
FIG. 3 indicates a setting with multiple M-Mode lines, according to an embodiment of this invention.

FIG. 3 illustrates an example where two tilted M-Mode displays 34A, 34B have been computed or calculated from a single 2D sequence or image 32, with corresponding virtual, tilted M-Mode lines indicated at 33A and 33B respectively. Basing the generation of M-Mode displays on 2D or 3D images, any sector number of M-Mode displays can be generated, enabling analysis of various dimensions from the same heartbeat. Thus, acquired time series as indicated at 1, 2, 3, 4 in FIG. 2 are arranged to constitute data sets, at least one virtual M-Mode line 23 or 33A, 33B in FIG. 3, are provided and co-registered with the data sets, and these are then subjected to computer processing with interpolation along the virtual M-Mode line concerned. The importance of interpolation will be explained further below.

MOTION CORRECTION

As the heart moves inside the chest during contraction and relaxation, a correct M-Mode line position at one point in the heart cycle may be wrong at another point in the same heart cycle. This is very difficult to compensate for manually, the probe must be moved synchronous to the heartbeats.

Figure 4:
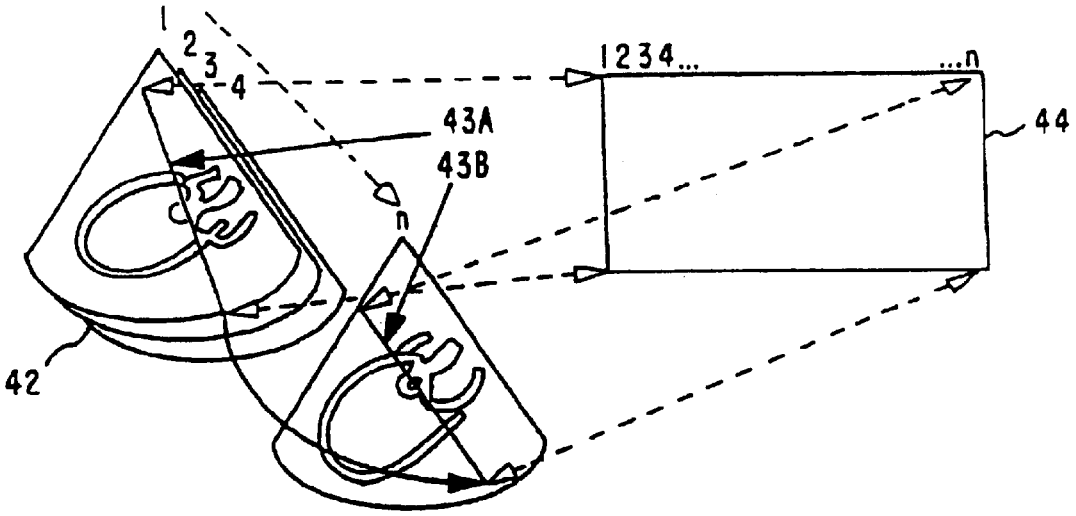
FIG. 4 illustrates how movement of the position of the M-Mode line as a function of the position in the cardiac cycle can be used to obtain motion correction.

The anatomical M-Modes according to this invention can compensate for this motion. FIG. 4 illustrates this concept. The user defines the position of the M-Mode line 43A and 43B respectively, at different points in the heart cycle such as by scrolling a 2D cineloop and fixing a new M-Mode line position. Appropriate computer operations or software are available and known to those of ordinary skill in this field, as shown in the above references, is utilized to interpolate the M-Mode line positions between the "fixed" M-Mode lines 43A and 43B, and generates an M-Mode display 44 where each vertical line in the M-Mode display is extracted along the local definition of the M-Mode line.

In this manner the position and/or orientation of the virtual M-Mode line can be movable in response to other rhythmic movements in the biological structure or body concerned, other than the heartbeats referred to in the description of FIG. 4.

MOTION REFERENCE POINTS

When studying an organ's time-variant dimensions in a living body, there is often a wish to study the different structures' dimensions relative to each other, without observing the whole organ's displacement inside the body. This is especially interesting when looking at the heart's ventricular contractions and relaxations, where the thickening of the muscle tissue is the important parameter to observe.

Figure 5:
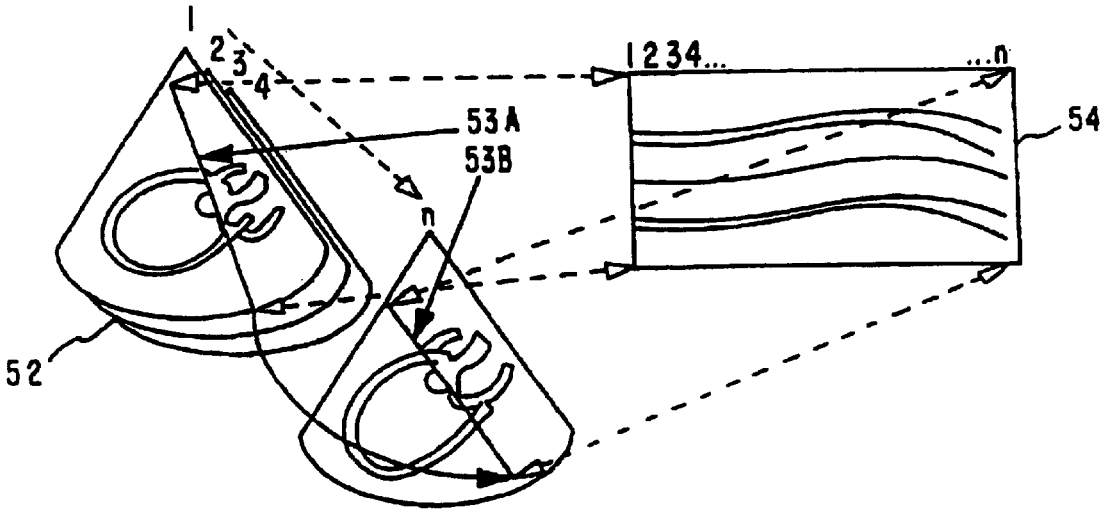
FIG. 5 illustrates an anatomical M-Mode whereby no reference point is specified.
Figure 6:
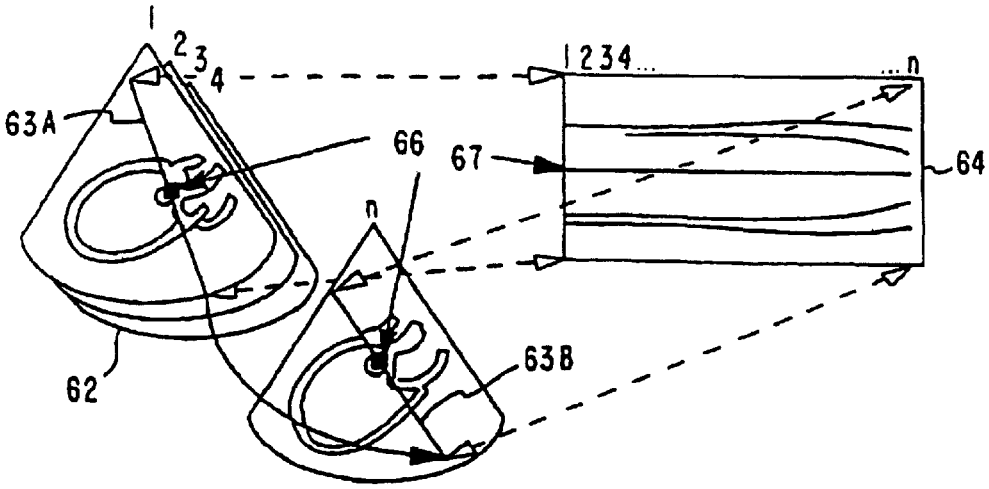
FIG. 6 illustrates an anatomical M-Mode line when a reference point has been specified and fixed to given vertical position in the display of the anatomical M-Mode.

To enhance the relative variations, according to an embodiment of this invention, the user can define a reference point on the "fixed" M-Mode lines described in the previous paragraph on motion correction. Typically, this point will correspond to an easily defined clinical structure. FIGS. 5 and 6 illustrate M-Mode generation without and with a fixation of a given reference point 66 in the imaged scene 62.

Thus, on the basis of the reference point 66 associated with the interpolated M-Mode line positions 63A to 63B shown in FIG. 6, there is generated a M-Mode display 64 with this point 66 appearing as a straight line 67 (no motion) i.e. at a chosen vertical coordinate in the display. Alternatively, a given y-coordinate can be tracked in the M-Mode display and the M-Mode display regenerated by sliding the position of the M-Mode lines at the various time locations such that the tracked image structure appears as a horizontal structure in the final M-Mode display.

WALL THICKENING ANALYSIS

Figure 7:
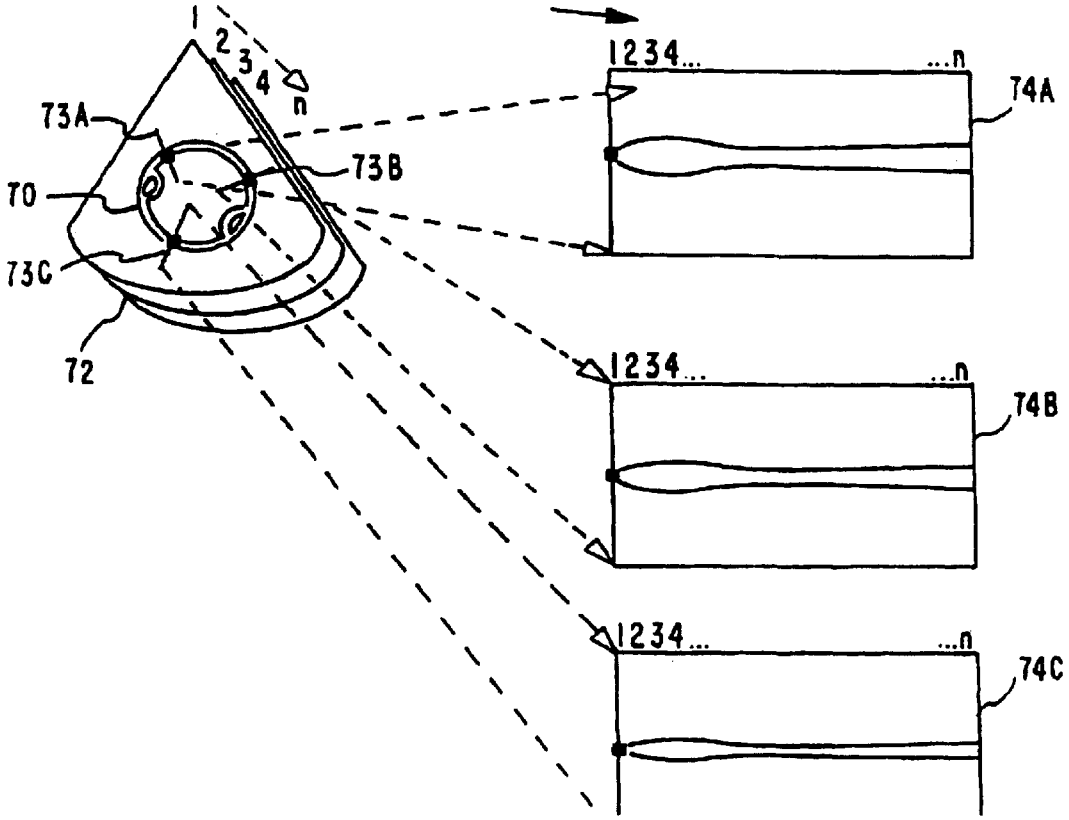
FIG. 7 illustrates wall thickening analysis in a setting with 3 simultaneous anatomical M-Mode displays.

With coronary diseases, an important parameter to observe is the thickening of the left ventricular muscle at various positions. Combining the techniques described in previous paragraphs, this invention provides a specially useful tool for left ventricle thickening analysis, as illustrated by FIG. 7.

Each M-Mode display 74A, 74B and 74C represents the regional wall thickening and contraction of one part of the ventricle 70, each part being penetrated by a corresponding virtual M-Mode line 73A, 73B and 73C respectively. FIG. 7 shows a short axis view of the left ventricle 70 and three anatomical M-Mode displays 74A, 74B, 74C generated with the techniques described in the previous paragraphs.

IMPLEMENTATION

Figure 8:
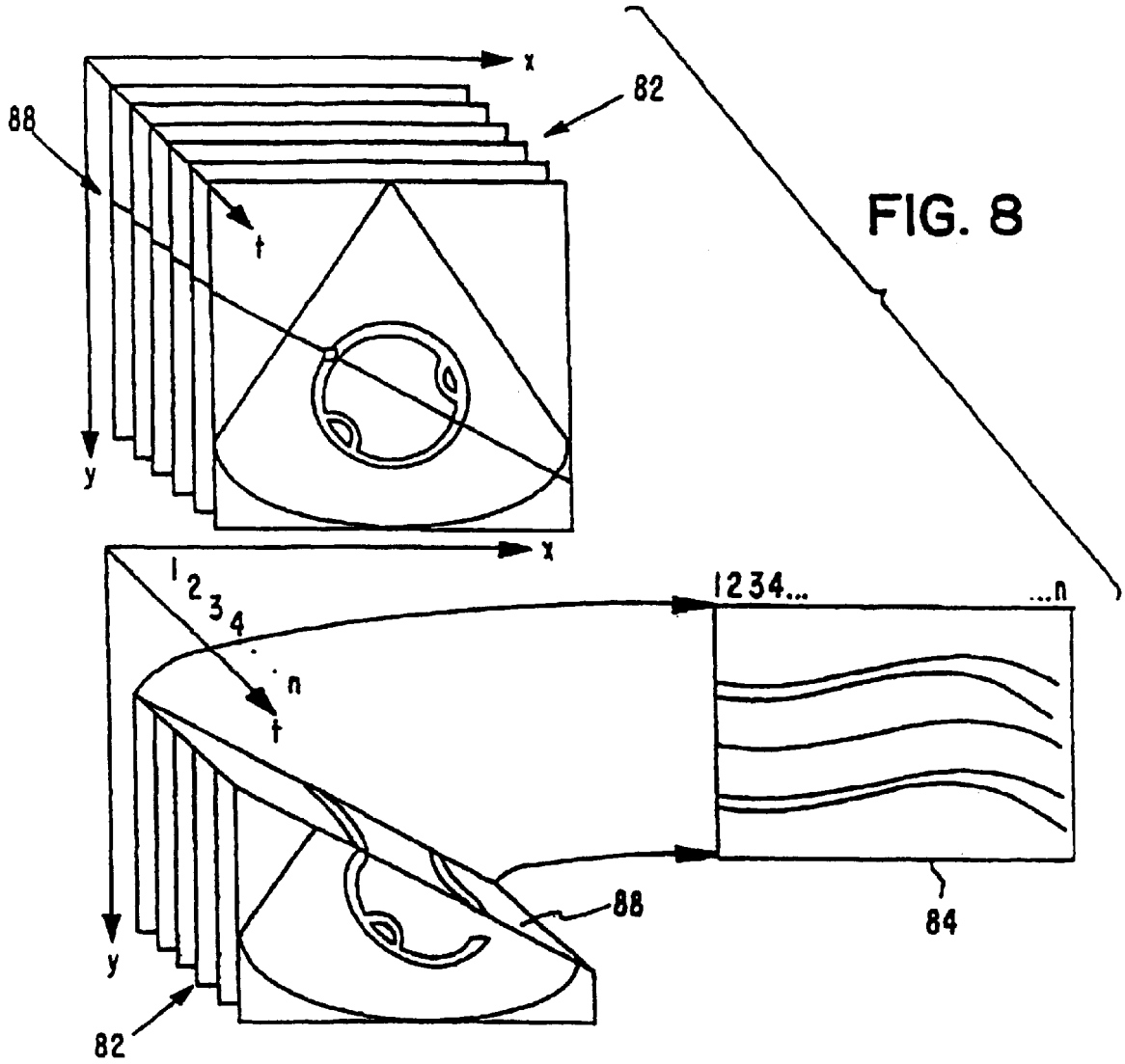
FIG. 8 indicates how the anatomical M-Mode displays are computed in a situation where the position of the M-Mode line is fixed during the cardiac cycle.

The sequence of 2D/3D frames is stored in the scanner/computer employed as a 3- or 4-dimensional array or data set(s) of ultrasound samples. This array may have different geometric properties, depending on the transducer probe geometry used, and whether images have been scanconverted to a rectangular format prior to storing. For illustration, in the setting shown in FIG. 8, we use an example where the 2D sector data have been scanconverted previously (typically using an ultrasound scanner's hardware scanconverter) and stored to disk/memory in a rectangular data set format, as a 3D-array 82 of samples with the dimensions being [x,y,t].

Generating an M-Mode display 84 can then be viewed upon as cutting a plane 88 through the 3D data set 82, interpolating and resampling the data to fit into the desired display rectangle 84. The motion correction techniques described above will modify the cutting plane 88 to a curved surface that is linear in the intersections with the [x,y] planes. It is of primary importance that adequate interpolation techniques are applied both in the spatial and temporal dimension. Such interpolation can to some extent compensate for inferior resolution compared with conventional M-Mode along the acoustical beams generated by the transducer as shown in FIG. 1.

Temporal resolution of the M-Mode displays may be increased by controlling the image acquisition to encompass only the necessary area. In FIG. 10, the virtual M-Mode line 101 defines the minimum necessary image area 104. By controlling the front-end of the ultrasound scanner to only acquire the necessary acoustical beams 102, and not acquiring the data 103 outside the virtual M-Mode line, the ultrasound scanner uses less time for acquiring the image, and this time is used to improve the temporal resolution of the time series. This special enhancement can be done at the cost of freely positioning other virtual M-Mode lines during post-processing.

According to an embodiment of the invention it is an additional and advantageous step to let the result of the above computer processing including interpolation, be subjected to an image processing as known per se for edge enhancement, to produce the resulting computed anatomical M-Mode display.

3D ULTRASONIC IMAGING

All the techniques described here apply both to a sequence of 2D and a sequence of 3D ultrasonic images. 3D acquisitions further improves the potential of motion correction described, because the true 3D motion of the heart can be estimated.

In addition to the actual generation of M-Mode displays the techniques according to this invention can be further utilized to extract anatomical M-Modes for all points across the endocard surface in the left ventricle. This setting is illustrated with an example in FIG. 9. A 4 dimensional ultrasound data set 92 is assumed consisting of m short axis planes and n 3D cubes recorded during the cardiac cycle. For simplicity in the figure only three virtual M-Mode lines 93A, 93B, 93C with the associated M-Mode displays 94A, 94B and 94C, respectively, have been drawn, but similar M-Mode displays should be associated with every point or position on the endocard surface in the ventricle 90.

Each of the individual M-Mode displays 94A, 94B, 94C . . . , are then processed in order to obtain a characterization that can be visualized as a color encoding of the associated location on the ventricle wall. The mapping strategy is illustrated in FIG. 9 and is similar to the approach found in ref. B. Olstad, "Maximizing image variance in rendering of volumetric data sets," Journal of Electronic Imaging, 1:245–265, July 1992 and E. Steen and B. Olstad, "Volume rendering in medical ultrasound imaging". Proceedings of 8th Scandinavian Conference on Image Analysis. Tromsø, Norway May 1993 identified previously. The characterization routine thus operates on an anatomical M-Mode display and generates a single value or a color index that reflects physiological properties derived in the M-Mode image. One of these properties is a quantification of wall thickening by estimation of thickening variations during the cardiac cycle. Each of the anatomical M-Mode displays 94A, 94B and 94C are in this case analyzed. The wall is located in the said M-Mode displays methods such as those described in Peter Seitz, "Optical Superresolution Using Solid State Cameras and Digital Signal Processing", Optical Engineering 27(7) July 1988 for superresolution edge localization at the various time instances in the M-Mode displays and the thickness variations are used to define the said estimated quantification of wall thickening. A second property is given by a characterization of the temporal signal characteristics at a given spatial coordinate or for a range of spatial coordinates in the M-Mode displays 94A, 94B and 94C.

A second alternative is to use only two cubes that are either temporal neighbors or that are located at End-Systole and End-Diastole. The associated M-Modes will in this case reduce to simply two samples in the temporal direction. This approach is more easily computed and will provide differential thickening information across the ventricle wall if the cubes are temporal neighbors. The wall thickening analysis is in this case a comparison of two one dimensional signals where thickenings can be estimated with the methods described in Peter Seitz, "Optical Superresolution Using Solid State Cameras and Digital Signal Processing", Optical Engineering 27(7) July 1988 for superresolution edge localization.

The color encodings described for 3D also applies to 2D imaging, but the color encodings are in this case associated with the boundary of the blood area in the 2D image. FIG.

7 illustrates such a 2D image sequence. The figure includes only three virtual M-Mode lines 73A, 73B and 73C with the associated M-Mode displays 74A, 74B and 74C, respectively, but similar M-Mode displays should be associated with every point or position on the endocard surface in the ventricle 70. Each of the individual M-Mode displays 74A, 74B and 74C are then processed with the same techniques as described above for the corresponding M-Mode displays 94A, 94B and 94C in the three-dimensional case.

The M-Mode lines in this embodiment of the invention are associated with each point or position identified on the surface of the ventricle wall and the direction is computed to be perpendicular to the ventricle wall. The direction of the local M-Modes are computed as the direction obtained in a 2- or 3-dimensional distance transform of a binary 2- or 3-dimensional binary image representing the position of the points on the ventricle wall. See ref. G. Borgefors, "Distance transformations in digital images", Computer vision, graphics and image processing 34, 1986, pp. 344–371 for information on a suitable distance transform.

In summary this invention as described above provides a method for computation of anatomical M-Mode displays based on a time series of 2D or 3D ultrasonic images. The method is used for the investigation of living biological structures during movement, for example a heart function. The main application will be in hospitals and the like. The anatomical M-Mode displays can be computed in real-time during the image acquisition or by postprocessing of a 2D or 3D cineloop. The anatomical M-Mode is derived as a virtual M-Mode measurement along an arbitrary tilted M-Mode line. Multiple, simultaneous M-Mode lines and displays can be specified. The arbitrary positioning of the M-Mode line allows for anatomically meaningful M-Mode measurements that are independent of acoustic windows that limit the positioning of M-Modes in the prior art. The positioning of the M-Mode line can be changed as a function of time to compensate for global motion. The M-Mode line can in this way be made perpendicular to the heart wall during the entire heart cycle. This property increases the value of M-Modes in wall thickening analysis because erroneous thickenings caused by inclined measurements can be avoided. Furthermore, reference points in the image scene can be fixed in the M-Mode display such that the visual interpretation of relative variations can be improved. In 3D cineloops the M-Modes can be computed locally at all points in the ventricle wall along M-Mode lines that are perpendicular to the endocard surface. These local M-Modes are exploited to assess wall thickening and to utilize these measurements in a color encoding of the endocard surface.

We claim:

1. A method for generating anatomical M-Mode displays in ultrasonic investigation of living biological structures during movement employing an ultrasonic transducer the method comprising the steps of:

acquiring a time series of ultrasonic images;

arranging said time series so as to constitute data sets obtained by multiple ultrasound beams;

providing at least one virtual M-Mode line positioned in relationship to said data sets so as not to coincide with any ultrasonic beam direction of said transducer;

subjecting said data sets to computer processing on the basis of said at least one virtual M-Mode line, whereby interpolation along said at least one virtual M-Mode line is effected using values from said multiple ultrasound beams; and displaying the resulting computed anatomical M-Mode display on a display unit.

2. The method according to claim 1, further comprising the step of moving the position and orientation of said at least one virtual M-Mode line in response to rhythmic movement of the biological structure.

3. The method according to claim 2, further comprising the step of associating a reference point with said ultrasonic images and fixing a corresponding reference point at a chosen vertical coordinate in the resulting anatomical M-Mode display based upon said reference point.

4. The method according to claim 3, employed for investigating the left ventricle wall of the heart, the method further comprising the steps of:

computing anatomical M-Modes associated with each position on the left ventricle wall surface in ultrasonic images so as to represent a differential time evolution of the cardiac cycle, and characterizing each of the computed anatomical M-Modes for color encoding at each said position on the left ventricle wall surface.

5. The method according to claim 3, further comprising the steps of:

computing anatomical M-Modes associated with each position on the left ventricle wall surface in ultrasonic images limited to the difference between two image frames, and characterizing each of the computed anatomical M-Modes for color encoding at each said position on the left ventricle wall surface.

6. The method according to claim 3, further comprising the steps of:

computing anatomical M-Modes associated with each position on the left ventricle wall surface in ultrasonic images so as to represent a time interval, and characterizing each of the computed anatomical M-Modes for color encoding at each said position on the left ventricle wall surface.

7. The method according to claim 1, employed for investigating the left ventricle wall of the heart, the method further comprising the steps of:

computing anatomical M-Modes associated with each position on the left ventricle wall surface in ultrasonic images so as to represent a differential time evolution of the cardiac cycle, and characterizing each of the computed anatomical M-Modes for color encoding at each said position on the left ventricle wall surface.

8. The method according to claim 7, further comprising the step of measuring local or global thickening of said left ventricle wall along said at least one virtual M-Mode line and utilizing the result of the measurement for said color encoding.

9. The method according to claim 7, further comprising the step of measuring temporal intensity variations along said at least one virtual M-Mode line and utilizing the result of the measurement for said color encoding.

10. The method according to claim 7, further including the step of determining the direction of said at least one virtual M-Mode line as the direction determined in the distance transform from an arbitrary position to the closest position on the left ventricle wall.

11. The method according to claim 1, further comprising the steps of:

computing anatomical M-Modes associated with each position on the left ventricle wall surface in ultrasonic images limited to the difference between two image frames, and characterizing each of the computed anatomical M-Modes for color encoding at each said position on the left ventricle wall surface.

12. The method according to claim 1, further comprising the steps of:

computing anatomical M-Modes associated with each position on the left ventricle wall surface in ultrasonic images so as to represent a time interval, and characterizing each of the computed anatomical M-Modes for color encoding at each said position on the left ventricle wall surface.

13. The method according to claim 12, further comprising the step of measuring local or global thickening of said left ventricle wall along said at least one virtual M-Mode line and utilizing the result of the measurement for said color encoding.

14. The method according to claim 12, further comprising the step of measuring temporal intensity variations along said at least one virtual M-Mode line and utilizing the result of the measurement for said color encoding.

15. The method according to claim 1, further comprising the step of subjecting the result of said computer processing with interpolation to image processing for edge enhancement, thus producing said resulting computed anatomical M-Mode display.

16. The method according to claim 1, wherein the step of acquiring a time series of ultrasonic images occurs after a desired virtual M-Mode line has been defined, such that only the ultrasound data necessary to generate the said virtual M-Mode line are acquired, thereby increasing the time-resolution of said time series and hence the said computed anatomical M-Mode display.

17. The method according to claim 1, further comprising the step of moving the position and orientation of said at least one virtual M-Mode line in response to rhythmic movement of the biological structure.

18. The method according to claim 1, further comprising the step of associating a reference point with said ultrasonic images and fixing a corresponding reference point at a chosen vertical coordinate in the resulting anatomical M-Mode display based upon said reference point.

19. The method according to claim 1, wherein said time series of ultrasonic images is three dimensional.

*20. An ultrasound imaging apparatus comprising:*

*a memory to store ultrasonic information associated with a set of ultrasound beams; and*

*a computer processing device, coupled to said memory, said processing device to generate a virtual M-mode line that is distinct from said ultrasound beams, and to generate image data based on said M-Mode line.*

*21. The apparatus of claim 20, wherein said virtual M-mode line is non-coincident with said set of ultrasound beams.*

*22. The apparatus of claim 21, further comprising:*

*a transducer, coupled to said memory, to provide said ultrasonic information associated with said set of ultrasound beams.*

*23. The apparatus of claim 21, further comprising:*

*a display, coupled to said processing device, to display an image based on said image data.*

*24. The apparatus of claim 23, wherein said image includes color encoded information, based on a predetermined variable.*

*25. The apparatus of claim 24, wherein said predetermined variable depends on temporal variation along said virtual M-mode line.*

*26. The apparatus of claim 24, wherein said predetermined variable depends on a thickness of an anatomical structure.*

*27. The apparatus of claim 26, wherein said structure comprises an anatomical structure having motion.*

*28. The apparatus of claim 21, wherein said ultrasonic information comprises a time series of ultrasonic information.*

*29. The apparatus of claim 21, wherein said processing device is operable to vary at least one of a position and an orientation of said virtual M-mode line.*

*30. The apparatus of claim 29, wherein said processing device is further operable to vary at least one of said position and said orientation of said virtual M-mode line based on motion of a structure indicated by said ultrasonic information.*

*31. A system for providing ultrasound imaging, said system comprising:*

*a first means for providing ultrasonic information based on a set of ultrasound beams; and*

*a second means for generating image data based at least in part on a virtual M-mode line means which is distinct from said ultrasound beams.*

*32. The system of claim 31, wherein:*

*said first means includes a transducer means for generating said set of ultrasound beams upon which said ultrasonic information is based; and*

*said M-mode line which is non-coincident with said set of ultrasound beams.*

*33. The system of claim 31, further comprising:*

*a display means for displaying an image associated with said image data.*

*34. The system of claim 33, wherein said image includes color encoded information, based on a predetermined variable.*

*35. The system of claim 34, wherein said predetermined variable depends on temporal variation with respect to said virtual reference means.*

*36. The system of claim 34, wherein said predetermined variable depends on a thickness of an anatomical structure.*

*37. The system of claim 31, wherein said ultrasonic information comprises a time series of ultrasonic information.*

*38. The system of claim 31, wherein said second means comprises means for varying at least one of a position and an orientation of said virtual M-mode line means.*

*39. The system of claim 38, wherein said second means provides for varying at least one of said position and said orientation of said virtual M-mode line means based on motion of a structure indicated by said ultrasonic information.*

*40. A method for use in an ultrasound imaging system, said method comprising:*

*storing ultrasonic data associated with a set of ultrasonic beams; and*

*generating a virtual M-mode line to generate image data based on said ultrasonic data, wherein said virtual M-mode line is distinct from said set of ultrasonic beams.*

*41. The method of claim 40, further comprising:*

*displaying an image based on an interpolation of said ultrasonic data along said reference.*

*42. The method of claim 41, further comprising:*

*color encoding said image based on a predetermined criteria.*

*43. The method of claim 42, wherein said predetermined criteria is associated with a temporal intensity variation*

*with respect to said virtual reference, which comprises a virtual M-mode line.*

*44. The method of claim 42, wherein said predetermined criteria is associated with thickening of an anatomical structure.*

*45. The method of claim 40, wherein said virtual M-mode line non-coincident with said set of ultrasound beams.*

*46. The method of claim 40, further comprising:*

*acquiring a time series of ultrasonic information; and*

*arranging said time series of ultrasonic information to generate said ultrasonic data, which represents data sets obtained by said set of ultrasonic beams.*

*47. The method of claim 46, wherein said time series of ultrasonic information is three-dimensional (3D).*

*48. The method of claim 40, further comprising:*

*moving at least one of a position and orientation of said virtual M-mode line.*

*49. The method of claim 48, wherein moving said at least one of said position and orientation of said virtual M-mode line depends on movement of an object represented by said ultrasonic data.*

*50. The method of claim 40, further comprising:*

*performing edge enhancement image processing upon said ultrasonic data; and*

*displaying an image based on said edge enhanced ultrasonic data, said image representing an interpolation of said ultrasonic data along said virtual M-mode line.*

* * * * *

UNITED STATES PATENT AND TRADEMARK OFFICE

CERTIFICATE OF CORRECTION

PATENT NO. : RE 37,088 E
APPLICATION NO. : 09/078378
DATED : March 6, 2001
INVENTOR(S) : Olstad et al.

It is certified that error appears in the above-identified patent and that said Letters Patent is hereby corrected as shown below:

Title Page; should read;
Item (64),
Cover Page: The Reissue Data is as follows:

"Patent No.: 5,515,856
Issued: May 14, 1996
Appl. No.: 08/379,205
Filed: Jan. 27, 1995".

Signed and Sealed this

Fourteenth Day of April, 2009

John Doll

JOHN DOLL
*Acting Director of the United States Patent and Trademark Office*